United States Patent
Doosa et al.

(10) Patent No.: US 10,654,773 B2
(45) Date of Patent: May 19, 2020

(54) INTEGRATED FLUID CATALYTIC CRACKING AND OXIDATIVE PROPANE DEHYDROGENATION PROCESS

(71) Applicant: INDIAN OIL CORPORATION LIMITED, Mumbai (IN)

(72) Inventors: Hima Bindu Doosa, Faridabad (IN); Ram Mohan Thakur, Faridabad (IN); Vineeth Venu Nath, Faridabad (IN); Kamlesh Gupta, Faridabad (IN); Debasis Bhattacharyya, Faridabad (IN); Sanjiv Kumar Mazumdar, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 16/175,630

(22) Filed: Oct. 30, 2018

(65) Prior Publication Data
US 2019/0194092 A1 Jun. 27, 2019

(30) Foreign Application Priority Data
Dec. 21, 2017 (IN) .............................. 201721046122

(51) Int. Cl.
*C07C 5/48* (2006.01)
*C07C 5/42* (2006.01)
*C07C 7/09* (2006.01)
*C07C 7/00* (2006.01)

(52) U.S. Cl.
CPC ................. *C07C 5/48* (2013.01); *C07C 5/42* (2013.01); *C07C 7/005* (2013.01); *C07C 7/09* (2013.01)

(58) Field of Classification Search
None
See application file for complete search history.

(56) References Cited

U.S. PATENT DOCUMENTS

| | | | |
|---|---|---|---|
| 4,337,145 A | 6/1982 | Tu | |
| 4,632,749 A | 12/1986 | Hilfman | |
| 4,788,371 A | 11/1988 | Imai et al. | |
| 5,846,402 A | 12/1998 | Mandal et al. | |
| 7,094,942 B2 | 8/2006 | Abdulwahed et al. | |
| 8,563,793 B2 | 10/2013 | Zimmermann et al. | |

(Continued)

OTHER PUBLICATIONS

Shishido, T., et al., "Role of CO2 in dehydrogenation of propane over Cr-based catalysts," Catalysis Today, vol. 185, Issue 1, pp. 151-156 (May 20, 2012).

*Primary Examiner* — Tam M Nguyen
(74) *Attorney, Agent, or Firm* — Maschoff Brennan (57) ABSTRACT

The present invention is related to an integrated process for enhancing the yields of propylene and other light olefins from Fluid catalytic cracking (FCC) process in combination with Oxidative propane dehydrogenation (OPDH) where in a hydrocarbon stream from Propylene recovery section consisting of propane predominantly, is converted to high value light olefins primarily $C_3$ and $C_2$ olefins by catalytic oxidative dehydrogenation using carbon dioxide from FCC flue gas exiting the regenerator. Several process configurations for the conversion of $C_3$ and $C_4$ alkanes to their respective alkenes separately or simultaneously by integrating with FCC are provided.

17 Claims, 5 Drawing Sheets

(56) References Cited

U.S. PATENT DOCUMENTS

| | | | | |
|---|---|---|---|---|
| 2004/0152586 | A1* | 8/2004 | Ou | B01J 23/002 502/64 |
| 2011/0184191 | A1* | 7/2011 | Menendez Sastre | B01J 8/0085 549/258 |
| 2013/0178682 | A1* | 7/2013 | Luo | B01J 23/825 585/660 |
| 2014/0018594 | A1* | 1/2014 | Palo | B01D 53/22 585/655 |
| 2014/0249339 | A1* | 9/2014 | Simanzhenkov | B01J 19/0046 585/252 |
| 2014/0296593 | A1* | 10/2014 | Zhu | C07C 4/06 585/310 |
| 2015/0232395 | A1* | 8/2015 | Nyce | C10G 9/00 518/705 |
| 2016/0168051 | A1* | 6/2016 | Palmas | B01J 8/28 585/635 |
| 2017/0204025 | A1* | 7/2017 | DiGiulio | C07C 5/48 |
| 2017/0369400 | A1* | 12/2017 | Hinoishi | C07C 5/48 |
| 2020/0063045 | A1* | 2/2020 | Cao | B01J 31/1815 |

* cited by examiner

INTEGRATED FLUID CATALYTIC CRACKING AND OXIDATIVE PROPANE DEHYDROGENATION PROCESS

FIELD OF THE INVENTION

This invention pertains to the processes for catalytic conversion of alkane to alkylenes and integration of the process with FCC. This invention in particular relates to oxidative dehydrogenation of propane, ethane, and butane(s), recovered from $C_3$ splitter of Propylene recovery unit (PRU) and $C_4$-separation section, respectively, in combination with $CO_2$ from flue gas of FCC regenerator. Desired outcome of this integrated process include enhanced yield of light olefins such as, propylene, ethylene, and butylenes with simultaneous reduction of $CO_2$ emissions.

BACKGROUND OF THE INVENTION

Global demand for light olefins such as propylene, butylene, and ethylene is rapidly increasing due to wide applications of their derivates in the field of consumer durables, packaging, automotive, construction, medical, etc. Conventional sources of propylene are steam cracking of light hydrocarbons and also fluid catalytic cracking (FCC). With the discovery of shale gas reserves, ethylene production has increased significantly by steam cracking of lighter feedstock while propylene or butylene is obtained as by-product. This has resulted in a gap between the supply and demand for propylene or butylene and thus, a huge increase in the prices of both. In such scenario, alternative routes for on-purpose propylene/butylene production such as propane/butane dehydrogenation, olefin metathesis and methanol to olefins (MTO) have become significant.

U.S. Pat. No. 8,563,793 describes an integrated process for recovery of propylene from the hydrocarbon stream consisting of propane and/or $C_4$-components, and catalytic dehydrogenation of propane to propylene, wherein purified propane fraction from PRU and recycled hydrogen stream are sent to dehydrogenation section to produce propylene. Dehydrogenation of propane (or any alkane) is an endothermic reaction and is limited by its thermodynamic equilibrium, due to which higher temperatures (usually above 600° C.) are required to achieve economically feasible conversions. Such high temperatures cause thermal cracking of hydrocarbons lowering selectivity of desired unsaturated hydrocarbon propene (or corresponding alkene) and accelerate catalyst deactivation. In order to maintain lower partial pressures of alkanes, the system is diluted with hydrogen stream which results in limited conversion and alkene selectivity.

Alkane dehydrogenation in the presence of oxygen can be performed at lower temperature. Moreover, the dehydrogenation equilibrium can be shifted forward to obtain higher alkane conversions by the reaction of oxygen with the hydrogen co-product. Oxygen is believed to burn the coke off the catalyst and thereby keep the surface clean from coke deposition, leading to increased catalyst life. U.S. Pat. No. 4,788,371 A discloses an oxidative dehydrogenation (ODH) process, wherein the alkane feed along with oxygen and steam is introduced into the reactor containing noble metal catalyst. The effect of oxygen here is to combust hydrogen with minimal combustion of hydrocarbons.

Alkenes produced by ODH process are easily oxidized in the presence of oxygen, and thus, the selectivity of alkenes decline rapidly with increase in conversion of alkanes. Another drawback of using oxygen as a promoter in dehydrogenation reaction is that, it requires special handling and explosive protection apparatus for its safe operation in commercial scale, since oxygen can form explosive mixtures with hydrocarbons. Therefore, mild oxidant such as carbon dioxide is extensively used to improve the propane conversion in oxidative dehydrogenation reactions with minimum effect on the propylene selectivity. Utilization of carbon dioxide in industrial process also helps in the mitigation of $CO_2$ from the atmosphere. $CO_2$ not only suppresses the unwanted total oxidation products due to its lower oxidizing ability, but also improves product selectivity. In the presence of carbon dioxide, the propane dehydrogenation proceeds in oxidative pathway whose rate of the reaction is faster than the direct dehydrogenation reaction thereby producing higher yield of propylene (T. Shishido et al., Catal. Today, 2012, 185, 151-156).

Numerous catalyst formulations for propane dehydrogenation using carbon dioxide have been disclosed. For example, U.S. Pat. No. 7,094,942 B2 describes the process where the alkanes are contacted with Cr-based dehydrogenation catalyst in the presence of $CO_2$ to produce corresponding alkenes at a temperature ranging from 400° C. to 700° C., a pressure ranging from 0.1 to 10 atm, wherein the alkane to $CO_2$ molar ratio is about 1:0.0001 to 1:0.045.

U.S. Pat. No. 182,186 A1 discloses the process for dehydrogenation of propane to propylene using a silica chromium catalyst composition in the presence of $CO_2$. Further, the silica Cr catalyst composition may include a promoter, such as, V, Ag, Ce, Zn, Zr, etc.

Reduction in emissions of greenhouse gases like carbon dioxide to the atmosphere is gaining momentum to combat the increasing global warming. Therefore, there exists a need for developing environmental friendly and cost-effective processes that utilize feed sources from existing refinery.

SUMMARY OF THE INVENTION

It is the primary objective of the invention to produce high valued alkenes from alkanes utilizing harmful greenhouse gases such as $CO_2$ as co-feed.

It is another objective of the invention to provide an economical integrated fluidized catalytic cracking (FCC) and Oxidative dehydrogenation process (ODH) process for the conversion of $C_3$ and $C_4$ alkanes to their respective olefins.

It is further objective of the invention to provide an efficient process utilizing the $C_3/C_4$ hydrocarbons from PRU and $CO_2$ from flue gas as feed components, and generate high-valued light olefins with simultaneous reduction of $CO_2$ emissions to atmosphere.

An embodiment of the present invention provides an integrated process for catalytic conversion of alkanes to alkenes, wherein an alkane stream from product recovery section of FCC process is converted to respective olefins by catalytic ODH, wherein the ODH process utilizes carbon dioxide from flue gas exiting from regenerator of the FCC process.

DESCRIPTION OF THE INVENTION

While the invention is susceptible to various modifications and/or alternative processes and/or compositions, specific embodiment thereof has been shown by way of example in tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The tables and protocols have been represented where appropriate by conventional representations, showing only those specific details that are pertinent to understanding the embodiments of the present invention so as not to obscure the disclosure with details that will be readily apparent to those of ordinary skill in the art having benefit of the description herein.

The following description is of exemplary embodiments only and is NOT intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Any particular and all details set forth herein are used in the context of some embodiments and therefore should NOT be necessarily taken as limiting factors to the attached claims. The attached claims and their legal equivalents can be realized in the context of embodiments other than the ones used as illustrative examples in the description below.

The present invention is associated with the integrated process involving Fluid Catalytic Cracking (FCC) and Catalytic Oxidative Propane Dehydrogenation processes, wherein, the propane obtained from $C_3$ splitter of propylene recovery section is converted into $C_2$, $C_3$ olefins by oxidative dehydrogenation reaction in presence of suitable catalyst, using carbon dioxide from flue gas exiting from FCC regenerator.

In an embodiment, the present invention provides an integrated process for catalytic conversion of alkanes to alkenes, wherein an alkane stream from product recovery section of FCC process is converted to respective olefins by catalytic ODH, wherein the ODH process utilizes carbon dioxide from flue gas exiting from regenerator of the FCC process. The integrated process enhances the yield of the propylene at $C_3$-splitter of the PRU, the butylenes yield at $C_4$-separation section and ethylene yield at ethylene recovery section by utilizing $CO_2$ from the FCC flue gas.

In a preferred embodiment of the present invention, the alkanes are at least one of ethane, propane, and butanes and the respective alkenes are at least one of ethylene, propylene, and butylenes.

In another preferred embodiment of the present invention, the process comprises of the following steps:
a) feeding cracked hydrocarbon products from FCC riser-reactor to a main fractionator column to obtain a product stream comprising of dry gas, LPG, and light naphtha,
b) separating the product stream in a gascon section, into LPG comprising of $C_3$ and $C_4$ hydrocarbons, and dry gas comprising of hydrogen, methane, ethane, ethylene, and other non-condensable gases,
c) routing the LPG stream to propylene recovery unit (PRU) to separate and obtain propane, wherein the propane is used as feed stream for ODH process,
d) subjecting the flue gas from FCC regenerator to carbon dioxide ($CO_2$) separation to recover $CO_2$, wherein the remaining flue gas is released to stack,
e) premixing the propane feed stream obtained from step (c) and the recovered $CO_2$ from step (d) and utilizing the mixture as feed for ODH process to obtain propylene, unreacted propane, ethylene, and other gases, and
f) re-routing the products from step (e) to the gascon section after separation of water.

In yet another preferred embodiment of the present invention, the process comprises of the following steps:
a) feeding cracked hydrocarbon products from FCC riser-reactor to a main fractionator column to obtain a product stream comprising of dry gas, LPG, and light naphtha,
b) separating the product stream in a gascon section, into LPG comprising of $C_3$ and $C_4$ hydrocarbons, and dry gas comprising hydrogen, methane, ethane, ethylene, and other non-condensable gases,
c) routing the dry gas to ethylene recovery section to separate and obtain ethane, wherein the ethane is used as a feed stream for ODH process,
d) subjecting the flue gas from FCC regenerator to carbon dioxide ($CO_2$) separation to recover $CO_2$, wherein the remaining flue gas is released to stack,
e) premixing the ethane feed stream obtained from step (c) and the recovered $CO_2$ from step (d) and utilizing the mixture as feed for ODH process to obtain ethylene, unreacted ethane, and other gases, and
f) re-routing the products from step (e) to the gascon section after separation of water.

In yet another preferred embodiment of the present invention, the process comprises of the following steps:
a) feeding cracked hydrocarbon products from FCC riser-reactor to a main fractionator column to obtain a product stream comprising of dry gas, LPG, and light naphtha,
b) separating the product stream in a gascon section, into LPG comprising of $C_3$ and $C_4$ hydrocarbons, and dry gas comprising hydrogen, methane, ethane, ethylene, and other non-condensable gases,
c) routing the LPG stream to propylene recovery unit (PRU) to separate and obtain $C_4$ hydrocarbon stream from debutanizer section,
d) routing the $C_4$ hydrocarbons to the $C_4$-separation section to separate and obtain $C_4$ alkanes comprising iso-butane and n-butane, wherein the iso-butane or n-butane or their mixture is used as feed stream for the ODH process,
e) subjecting the flue gas from FCC regenerator to carbon dioxide ($CO_2$) separation to recover $CO_2$, wherein the remaining flue gas is released to stack,
f) premixing the $C_4$ feed stream obtained from step (d) and the recovered $CO_2$ from step (e) and utilizing the mixture as feed for ODH process to obtain butylenes, unreacted butane(s), $C_2$, $C_3$, and other hydrocarbons, g) re-routing the products from step (f) to the gascon section after separation of water.

In another preferred embodiment of the present invention, the process comprises of the following steps:

a) sending the flue gas from the FCC regenerator to $CO_2$ recovery unit for $CO_2$ separation, wherein the remaining flue gas is released to stack, b) mixing the $CO_2$ gas with the $C_3$ hydrocarbon product from the PRU and sending the resultant gas mixture to a propane dehydrogenation (PDH) reactor to produce propylene, wherein the feed gas mixture is pre-heated by PDH reactor effluent stream, and c) mixing the $CO_2$ gas with $C_4$ alkanes from $C_4$-separation section and sending the resultant gas mixture to a butane dehydrogenation (BDH) reactor to produce butylenes, wherein the feed gas mixture is pre-heated by BDH reactor effluent stream.

d) Continuous circulation of catalyst from PDH reactor to BDH reactor and then to catalyst regeneration unit; re-circulating the hot catalyst to PDH reactor e) re-routing the products from step (b) and step (c) to the gascon section after separation of water In another embodiment of the present invention, the alkane feed stream from the PRU is mixed with hot flue gas from first stage regenerator of resid FCC unit and the mixture is directly used as feed for ODH reactor to obtain a product stream comprising of hydrocarbons and non-condensable gases.

In another embodiment of the present invention, the alkanes for dehydrogenation in the ODH process are selected from of at least one of the combinations of ethane and propane; propane and $C_4$ alkanes; ethane and $C_4$ alkanes; or ethane, propane, and $C_4$ alkanes.

In yet another embodiment of the present invention, the feed mixtures comprise of at least one of ethane/$CO_2$, propane/$CO_2$, iso-butane/$CO_2$, and n-butane/$CO_2$. In another embodiment of the present invention, the feed mixtures optionally comprise of diluents selected from steam, nitrogen or helium or a combination thereof.

In an embodiment of the present invention, the FCC process is at least one of fluid catalytic cracking or Resid fluid catalytic cracking or High severity fluid catalytic cracking or High severity propylene maximizing fluid catalytic cracking process. In another embodiment of the present invention, the ODH reactor is selected from at least one of fixed bed or fluidized bed or moving bed or combination thereof.

In yet another embodiment of the present invention, the heat from the flue gas exiting the FCC regenerator is utilized to pre-heat the ethane/$CO_2$, propane/$CO_2$, iso-butane/$CO_2$, and n-butane/$CO_2$ feed stream prior to sending to ODH reactor. In another embodiment of the present invention, the heat from the products exiting the dehydrogenation reactor is utilized to pre-heat at least one of ethane/$CO_2$, propane/$CO_2$, iso-butane/$CO_2$, and n-butane/$CO_2$ feed stream.

In another embodiment of the present invention, oxygen from the flue gas stream is removed in oxygen separation unit and oxygen-free flue gas stream is mixed with the at least one of ethane propane or butane feed stream prior to sending to ODH reactor.

In yet another embodiment of the present invention, the product stream is optionally routed to carbon monoxide (CO) recovery unit for separation of CO, wherein the CO deficient stream is recycled to the FCC gascon section.

In another embodiment of the present invention, the dehydrogenation of ethane, propane and butanes is carried out in ODH process, wherein the $C_2$, $C_3$ and $C_4$ alkanes are separately introduced at different zones of a fluidized bed riser type of reactor, with continuous catalyst regeneration.

In yet another embodiment of the present invention, the process comprises the following steps:

a) sending the flue gas from the FCC regenerator to $CO_2$ recovery unit for $CO_2$ separation, wherein the remaining flue gas is released to stack, b) mixing the $CO_2$ gas with the $C_3$ hydrocarbon product from PRU and sending to resultant gas to the fluidized bed riser type of reactor;

c) mixing the $CO_2$ gas with $C_4$ alkanes from $C_4$-separation section and sending to the fluidized bed riser type of reactor;

d) introducing the $C_2$, $C_3$, and $C_4$, alkanes separately at different zones of the fluidized bed riser type of reactor to produce propylene, ethylene, and butylene;

e) continuous circulation of catalyst from the reactor to catalyst regeneration unit;

f) re-circulating the hot catalyst to the reactor.

Process Scheme

According to an embodiment of the present invention, the process of the present invention is exemplified by, but not limited to the following figures.

Figure 1:
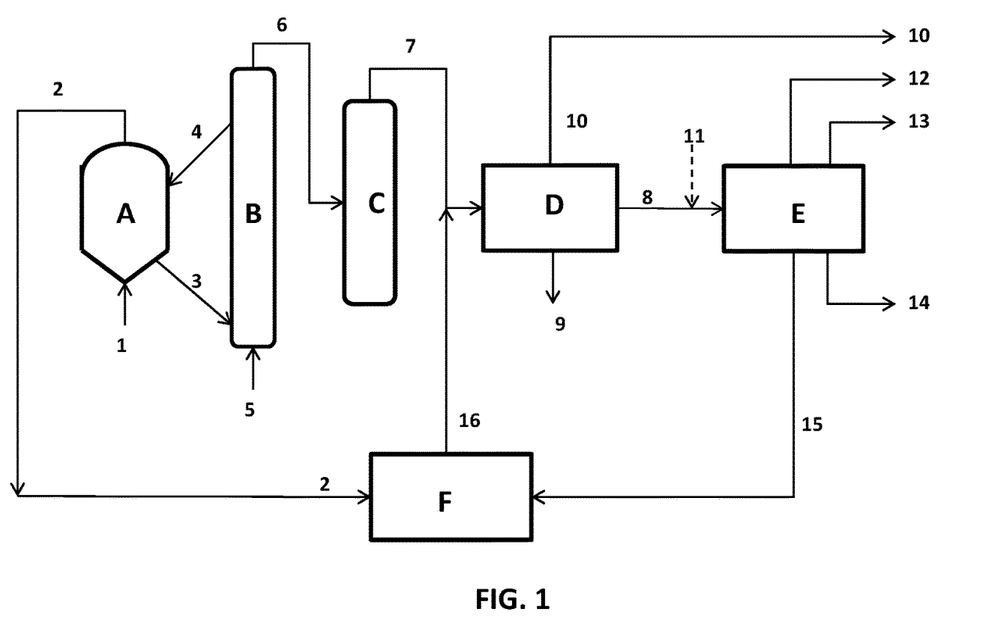
FIG. 1: Represents schematic flow diagram of integrated process involving Fluid Catalytic Cracking (FCC) and Catalytic Oxidative Propane Dehydrogenation

In accordance to an embodiment of the present invention, FIG. 1 provides schematic process flow diagram of the invented integrated process. FCC feedstock (5) constituting heavier or lighter hydrocarbon streams such as Vacuum gas oil (VGO) or hydrotreated VGO or reduced crude oil (RCO) or short residue (SR) or any other heavy or light hydrocarbon streams including naphtha or combination thereof is cracked in a riser-reactor (B) using zeolite catalyst to produce lighter hydrocarbons such as dry gas, LPG, gasoline, etc. During the cracking process, the catalyst gets deactivated by the deposition of coke and the deactivated catalyst (4) is sent to regenerator (A) where the coke is burnt off in the presence of air (1). Thus regenerated catalyst (3) is re-circulated back to the riser and the process continues. The flue gas (2) exiting the regenerator comprises of nitrogen, carbon dioxide and other gases. The FCC process is described in detail, elsewhere in patents, such as, U.S. Pat. Nos. 4,632,749, 4,337,145, 5,846,402 etc.

In another embodiment of the present invention, the cracked hydrocarbon products (6) from FCC riser-reactor are sent to the main fractionator column (C) where the fractions such as gasoline, heavy naphtha, light cycle oil (LCO), and clarified oil (CLO) are separated. The product stream (7) obtained from top section of main fractionator comprising of dry gas ($C_1$-$C_2$), LPG ($C_3$-$C_4$), light naphtha (9) and other products are separated in gascon section (D) followed by PRU section (E). The dry gas (10) comprising of hydrogen, methane, ethane, ethylene and other non-condensable gases is sent to ethylene recovery section. The $C_3$ LPG stream (8) is sent to propylene recovery unit (E) for further separation and recovery of petrochemical grade propylene (13). The feed of PRU includes $C_3$ stream from other sources (11), such as, delayed coker unit, hydrocracking unit, AVU, etc. Lean LPG (14) containing $C_4$ hydrocarbons and, fuel gas (12) are obtained as by-products of PRU. The bottom product (15) obtained from PRU $C_3$ splitter consisting of propane predominantly, is used as feed for oxidative PDH process (F) along with the FCC regenerator flue gas (2). The product stream (16) from OPDH process, mainly consisting of propylene, unreacted propane, ethylene and other gases is recycled back to the FCC gascon section for further separation. This integration of OPDH process with FCC unit enhances the propylene yield at $C_3$-splitter of PRU with simultaneous increase in the ethylene yield at ethylene recovery section. By using $CO_2$ in the integrated process, dehydrogenation reaction cycle time is enhanced.

Figure 2:
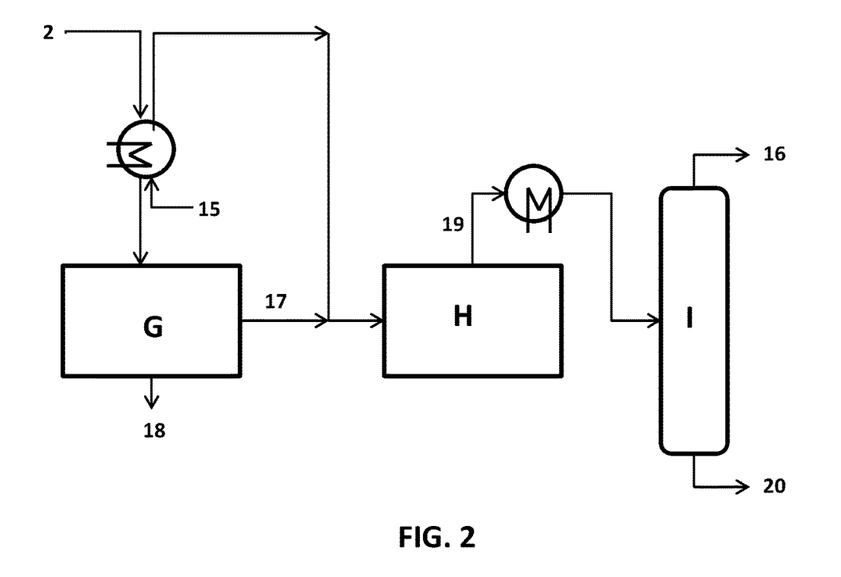
FIG. 2: Represents schematic flow diagram of oxidative propane dehydrogenation (OPDH) process

In accordance to an another embodiment of the present invention, FIG. 2 illustrates the representative of oxidative propane dehydrogenation (OPDH) process that is used in the integrated process scheme shown in FIG. 1, wherein, the flue gas from FCC regenerator, comprising of ~80 vol % of Nitrogen, ~15 vol % of $CO_2$, and small amounts oxygen and CO, is subjected to $CO_2$ separation and the recovered $CO_2$ is then used in oxidative dehydrogenation process as co-feed along with propane from PRU to produce propylene which is finally routed to gascon section of FCC after separation of water.

In an embodiment of the present invention, the heat from the flue gas (2) exiting the FCC regenerator (at >600° C.) is utilized to pre-heat the hydrocarbon (propane) feed stream (15). The cooled flue gas is routed to $CO_2$ recovery section (G) wherein the $CO_2$ is separated from flue gas by absorption or adsorption or cryogenic separation or membrane separation technique. The recovered $CO_2$ stream (17) from the $CO_2$ recovery unit is pre-mixed with the pre-heated $C_3$ hydrocarbons at a specific molar ratio and routed to the reactor (H) for catalytic dehydrogenation of propane. The feed mixture is sent directly or may contain diluents such as steam, nitrogen or helium or a combination thereof. The remaining flue gas stream (18) after $CO_2$ recovery is released to stack. Oxidative propane dehydrogenation is carried out in fixed bed reactor or fluidized bed reactor or moving bed reactors in series or a combination thereof using a metal catalyst on a suitable support. Since the reaction is endothermic, an external heat source is used to heat the reactant to desired temperature in the range of 500-700° C. The heat from the product stream (19) exiting the OPDH reactor is used for steam/power generation. The reactor effluent is compressed, cooled, and then sent to a separator (I) to condense the water (20) in the product stream. The top product (16) of the separator mainly consisting of propylene, unreacted propane, ethylene, methane and other gases is routed to the gascon section of FCC (as shown in FIG. 1) in order to obtain enhanced yield of propylene at the $C_3$ splitter of PRU.

Figure 3:
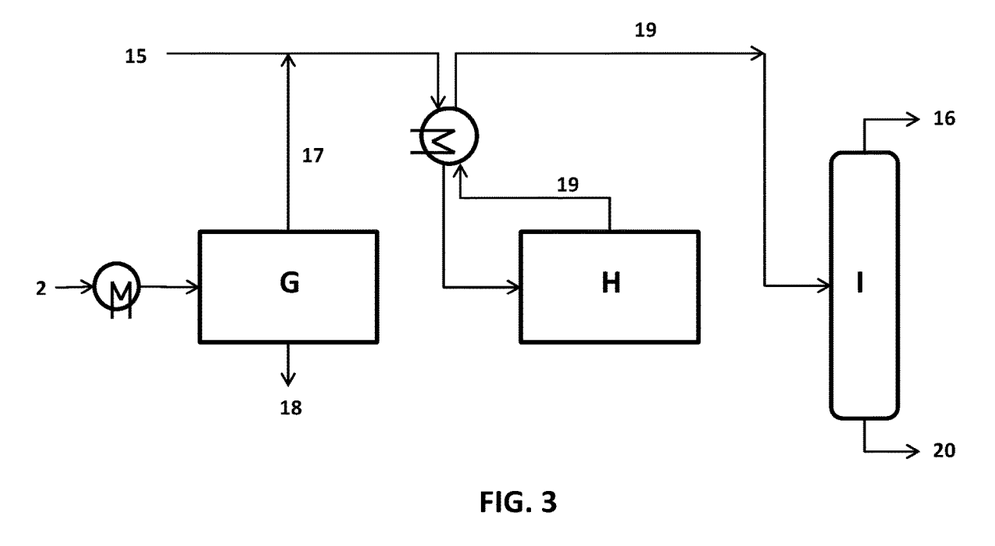
FIG. 3: Represents schematic flow diagram of an alternative configuration for oxidative propane dehydrogenation process

In another embodiment of the present invention, an alternative configuration for oxidative propane dehydrogenation process (described in FIG. 2) is represented in FIG. 3. After the heat extraction from flue gas exiting the FCC regenerator (2), it is sent to $CO_2$ recovery unit (G) where the $CO_2$ is separated by any of the methods mentioned in the above section. The flue gas stream (18) after $CO_2$ recovery is released to stack. The $CO_2$ enriched gas (17) is mixed with the $C_3$ hydrocarbon product (15) from PRU at a certain molar ratio and the resultant gas mixture is pre-heated by the OPDH reactor effluent stream (19) using a heat exchanger. The preheated feed mixture is sent directly or with the addition of diluent, to the reactor (H) for the conversion of propane to propylene. The cooled reactor effluent is routed to separator (I) to condense water (20). The top product (16) of the separator mainly consisting of propylene, un-reacted propane, ethylene, methane and other gases is routed to the gascon section of FCC (as illustrated in FIG. 1) in order to achieve higher propylene yield at the $C_3$ splitter.

In an embodiment of the present invention, propylene yield from the dehydrogenation reactor can be further enhanced in the presence of diluents such as, steam, helium, nitrogen, etc. Since the production of steam is energy consuming, the nitrogen from the regenerator flue gas can be utilized for this purpose. When the flue gas from regenerator is directly mixed with hydrocarbons at high temperatures, it may form an explosive mixture, due to the presence of oxygen. Therefore, it is required to remove oxygen from the flue gas before utilizing for OPDH process. The schematic for this process is elucidated by FIG. 3 (or FIG. 2), where the oxygen (18) from the flue gas stream (2) is removed in Oxygen separation unit (G), by catalytic oxidation process or adsorption on solid scavengers or any other suitable separation process. The oxygen free flue gas (17) is mixed with the $C_3$ hydrocarbon stream (15) from PRU, and the gas mixture is pre-heated by the OPDH reactor effluent stream (19) using a heat exchanger. The preheated feed mixture is sent directly to the reactor (H) without the addition of diluent, where propylene is produced by dehydrogenation of propane in the presence suitable catalyst by oxidative dehydrogenation reaction. The cooled reactor effluent is routed to a separator (I) for the removal of water (20) formed during the reaction and the remaining product (16) is recycled back to the gascon section of FCC, as shown in FIG. 1.

Figure 4:
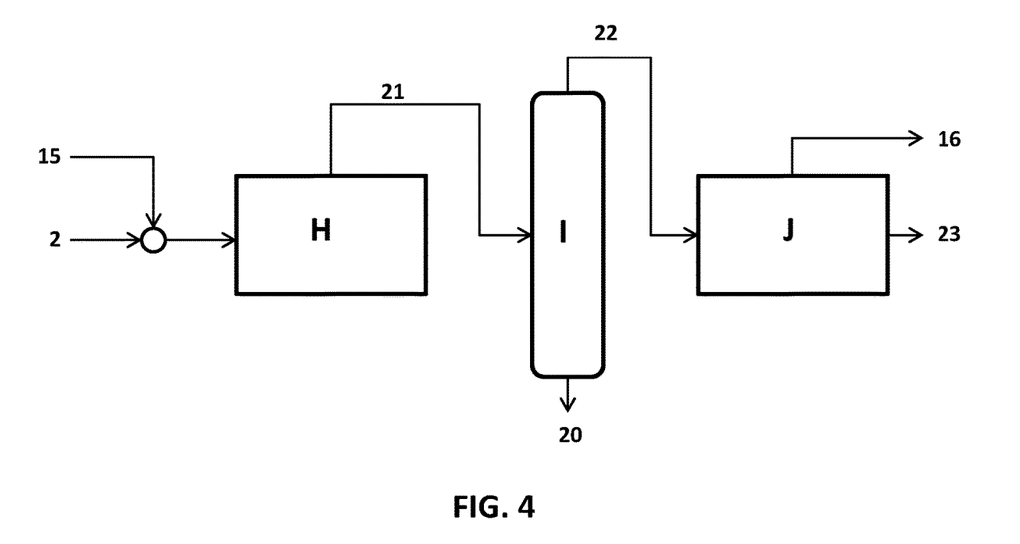
FIG. 4: Represents schematic flow diagram of an alternative configuration for oxidative propane dehydrogenation process

In another embodiment of the present invention, the flue gas from first stage regenerator of two stage Resid fluid catalytic cracking (RFCC) process comprising ~80 vol % nitrogen, ~10 vol % carbon monoxide (CO) and ~10 vol % carbon dioxide ($CO_2$) is directly used as co-feed for oxidative dehydrogenation of propane obtained from PRU section. The schematic for the same is depicted in FIG. 4. The major advantage of this process is to avoid the pre-treatment of the flue gas by either $CO_2$ recovery or $O_2$ removal.

In yet another embodiment of the present invention, the $C_3$ hydrocarbon stream (15) from PRU is pre-mixed with the hot flue gas (2) obtained from first stage regenerator of FCC and the resultant mixture is sent to the reactor (H) for oxidative propane dehydrogenation. The heat from the product stream (21) is utilized as discussed in above sections and the products are compressed, cooled, with subsequent separation (I) of water (20) formed during the reaction. The product stream (22) comprising of hydrocarbons along with non-condensable gases, such as, hydrogen, carbon monoxide, carbon dioxide and nitrogen, is routed to CO recovery unit (J) where the carbon monoxide (23) is separated by well-established techniques, such as, absorption in solvent containing cuprous aluminum chloride ($CuAlCl_4$), membrane separation, pressure swing adsorption, or any other suitable method. The CO deficient hydrocarbon stream (16) is recycled back to the FCC gas con section in order to achieve higher yield of propylene at the propane/propylene splitter of PRU. The purified CO can be utilized in methanol synthesis, DME synthesis, Fischer tropsch process and other applications. Alternatively, the product stream (22) can be directly routed to FCC gascon section.

Figure 5:
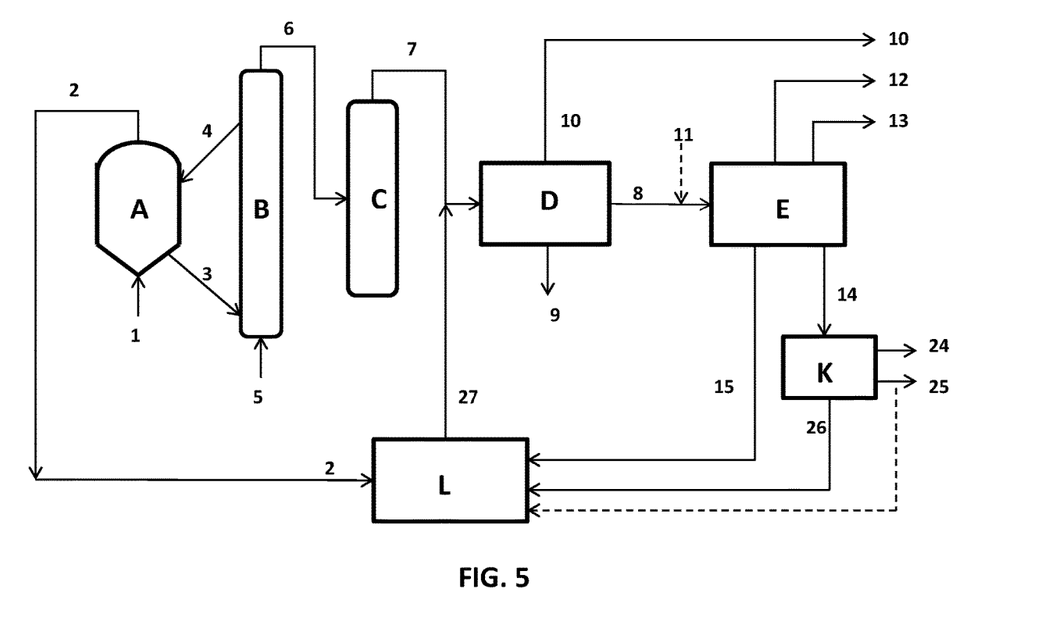
FIG. 5: Represents schematic flow diagram of integrated process for FCC and oxidative dehydrogenation (ODH) of propane and/or iso-butane and/or n-butane

In accordance to an embodiment of the present invention, FIG. 5 represents an integrated process for FCC and oxidative dehydrogenation (ODH) of propane and/or iso-butane. The description of the schematic in FIG. 5 is similar to of FIG. 1, except that the lean LPG stream (14) from PRU (E) comprising mainly of 1-butene, iso-butane and n-butane, is sent to $C_4$ hydrocarbons separation section (K), where iso-butane (26) is separated from other $C_4$ components, and sent to the oxidative dehydrogenation process (L) either along with or without propane (15), and flue gas (2) to produce propylene/iso-butylene. Alternatively, N-butane (25) recovered from $C_4$ hydrocarbons separation section (K) is co-fed with other reactants to ODH process (L) to obtain butenes and butadienes. Any commercially available technology can be adopted for the separation of individual $C_4$ hydrocarbon components. Other products from $C_4$ separation section (K)

include iso-butylene (24), 1-butene, 2-butene, 1,3 butadiene, etc. Butene-1 and iso-butylene are important raw materials of petrochemical and polymer industry. The effluent (27) of ODH process comprising of $C_2$, $C_3$, $C_4$ hydrocarbons and other gases is routed to FCC gascon section. This novel integrated process not only enhances the propylene yield at $C_3$-splitter of PRU but also improves the iso-butylene yield at $C_4$-separation section and ethylene yield at ethylene recovery section significantly, by utilizing carbon dioxide from FCC flue gas.

In another embodiment of the present invention, the dehydrogenation of propane, iso-butane and n-butane is carried out simultaneously or separately in fixed bed reactor or fluidized bed reactor or moving bed reactors in series or a combination thereof using a metal catalyst on a suitable support. In the case where propane, iso-butane and n-butane are pre-mixed, the schematic for combined oxidative dehydrogenation process (L) remain same as shown in FIGS. 2, 3 and 4. Alternatively, in a fluidized bed reactor system with continuous catalyst regeneration, the $C_3$ and $C_4$ alkanes are separately introduced into the riser type of reactor at different locations such that higher olefin selectivities are obtained. This type of reactor set-up is suitable for the dehydrogenation process in the presence or absence of $CO_2$.

Figure 6:
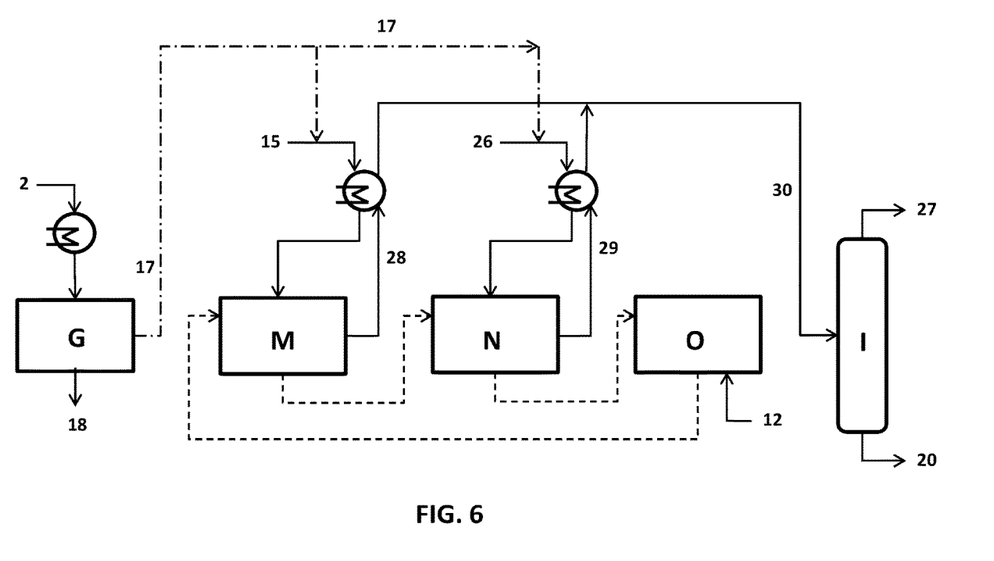
FIG. 6: Represents schematic flow diagram of oxidative dehydrogenation (ODH) process of propane and iso-butane

In accordance to an embodiment of the present invention, FIG. 6 represents ODH process (L), wherein the dehydrogenation of propane and iso-butane occurs simultaneously in separate reactors on a suitable catalyst which circulates (shown as dashed line) from reactor M to reactor N followed by catalyst regeneration unit (O). The regenerated catalyst is re-circulated to reactor M. Catalyst regeneration is performed using air or oxygen or steam or a combination thereof.

In another embodiment of the present invention, the flue gas from FCC regenerator (2) is sent to $CO_2$ recovery unit (G), where the $CO_2$ is separated by absorption or adsorption or cryogenic separation or membrane separation technique. The flue gas stream (18) after $CO_2$ recovery is released to stack. The $CO_2$ enriched gas (17, shown as dash dot line) is mixed with the $C_3$ hydrocarbon product (15) from PRU at a certain molar ratio and the resultant gas mixture is pre-heated by the propane dehydrogenation reactor (M) effluent stream (28) and sent to reactor M for the conversion of propane to propylene. Similarly, the iso-butane (26) from $C_4$-separation section (K) is mixed with the $CO_2$ enriched gas stream (17, shown as dash dot line) and the mixture is pre-heated by the butane dehydrogenation reactor (N) effluent stream (29) and sent to the reactor for the production of iso-butylene. Alternatively, the iso-butane and $CO_2$ mixture stream is pre-heated by the flue gas exiting the FCC regenerator. The feed mixtures propane/$CO_2$ and iso-butane/$CO_2$ are sent directly or may contain diluents such as steam, nitrogen or helium or a combination thereof.

Since the propane dehydrogenation reaction is endothermic, the temperature of the catalyst decreases as it moves from reactor M to reactor N. After iso-butane dehydrogenation in reactor N, the catalyst is sent to catalyst regeneration unit (O) where its temperature is increased by the oxidation of coke or combustion of fuel gas (12) obtained from PRU (FIG. 5) or a combination thereof. The hot catalyst is re-circulated to the reactor M. The combined product (30) from both the reactors is sent to separator (I) for the removal of water (20) and the remaining hydrocarbon stream (27) containing C2, C3, C4 hydrocarbons along with other gases is routed to FCC gascon section as shown in FIG. 5. The major advantage of simultaneous dehydrogenation of propane and iso-butane (FIG. 6) is its low requirement of energy since no additional intermittent heaters are required for heating feed or catalyst. Also, the temperature and residence time of the catalyst in each reactor is maintained such that optimum selectivities of propylene and iso-butylene are obtained.

Examples

The present invention is exemplified by following non-limiting example and tables.

Table 1-3, illustrates the product yield data of the integrated FCC-OPDH process compared with the FCC plant data from various sources and the component wise % enhancement in yields with its integration with OPDH process:

TABLE 1

| Component | Yield (wt %) | | |
| --- | --- | --- | --- |
| | Source: FCC plant data | Integrated process | Enhancement in yield (%) |
| Hydrogen | 0.02 | 0.05 | 160.65 |
| Ethylene | 1.12 | 1.24 | 10.38 |
| Propylene | 9.87 | 10.59 | 7.25 |
| Propane | 2.16 | 1.01 | |

It is evident from the Table 1 above, in comparison to conventional FCC process, the yield of hydrogen is enhanced by 160.65%, ethylene by 10.38%, and propylene by 7.25% on using the integrated process of the present invention.

TABLE 2

| Component | Yield (wt %) | | |
| --- | --- | --- | --- |
| | Source: RFCC plant data | Integrated process | Enhancement in yield (%) |
| Hydrogen | 0.06 | 0.10 | 63.72 |
| Ethylene | 0.85 | 0.99 | 16.28 |
| Propylene | 8.26 | 9.11 | 10.31 |
| Propane | 2.66 | 1.20 | |

It is evident from the Table 2 above, in comparison to conventional RFCC process, the yield of hydrogen is enhanced by 63.72, ethylene by 16.28%, and propylene by 10.31% on using the integrated process of the present invention.

TABLE 3

| Component | Yield (wt %) | | |
| --- | --- | --- | --- |
| | Source: Advanced RFCC process- max. Propylene mode | Integrated process | Enhancement in yield (%) |
| Hydrogen | 0.11 | 0.17 | 54.23 |
| Ethylene | 5.57 | 5.79 | 3.88 |
| Propylene | 20.30 | 21.63 | 6.54 |
| Propane | 4.01 | 1.87 | |

It is evident from the Table 3 above, in comparison to advanced RFCC process in propylene, the yield of hydrogen is enhanced by 54.23%, ethylene by 3.88%, and propylene by 6.54% on using the integrated process of the present invention.

The Tables 1-3 illustrating the comparable yield data between above confirms that the yield of hydrogen, ethylene, and propylene is enhanced on using integrated process of the present invention in comparison to convention FCC, RFCC, and advanced RFCC processes.

Those of ordinary skill in the art will appreciate upon reading this specification, including the examples contained herein, that modifications and alterations to the composition and methodology for making the composition may be made within the scope of the invention and it is intended that the scope of the invention disclosed herein be limited only by the broadest interpretation of the appended claims to which the inventor is legally entitled.

The invention claimed is:

1. An integrated process for catalytic conversion of alkanes to alkenes, wherein an alkane feed stream from recovery section of fluidized catalytic cracking (FCC) process is converted to respective olefins by catalytic oxidative dehydrogenation (ODH),
   wherein dehydrogenation of different alkanes occurs simultaneously in separated ODH reactors connected in series or in same ODH reactor with continuous catalyst regeneration; and
   wherein oxygen from flue gas exiting from a regenerator of the FCC process is removed in an oxygen separation unit to obtain an oxygen-free flue gas; and
   wherein the oxygen-free flue gas is mixed with the alkane feed stream prior to feeding to ODH reactor.

2. The process as claimed in claim 1, wherein the process comprises:
   a) feeding cracked hydrocarbon products from FCC riser-reactor to a main fractionator column to obtain a product stream comprising of dry gas, LPG, and light naphtha,
   b) separating the product stream in a gascon section, into LPG comprising of $C_3$ and $C_4$ hydrocarbons, and dry gas comprising of hydrogen, methane, ethane, ethylene, and other non-condensable gases,
   c) routing the LPG stream to propylene recovery unit (PRU) to separate and obtain propane, wherein the propane is used as feed stream for ODH process,
   d) subjecting the flue gas from FCC regenerator to oxygen ($O_2$) separation to obtain the oxygen-free flue gas,
   e) premixing the propane feed stream obtained from step (c) oxygen-free flue gas from step (d) and utilizing the mixture as feed mixture for ODH process to obtain propylene, unreacted propane, ethylene, and other gases, and
   f) re-routing the products from step (e) to the gascon section after separation of water.

3. The process as claimed in claim 1, wherein the process comprises:
   a) feeding cracked hydrocarbon products from FCC riser-reactor to a main fractionator column to obtain a product stream comprising of dry gas, LPG, and light naphtha,
   b) separating the product stream in a gascon section, into LPG comprising of $C_3$ and $C_4$ hydrocarbons, and dry gas comprising hydrogen, methane, ethane, ethylene, and other non-condensable gases,
   c) routing the dry gas to ethylene recovery section to separate and obtain ethane, wherein the ethane is used as a feed stream for ODH process,
   d) subjecting the flue gas from FCC regenerator to oxygen ($O_2$) separation to obtain the oxygen-free flue gas,
   e) premixing the ethane feed stream obtained from step (c) and the oxygen-free flue gas from step (d) and utilizing the mixture as feed mixture for ODH process to obtain ethylene, unreacted ethane, and other gases, and
   f) re-routing the products from step (e) to the gascon section after separation of water.

4. The process as claimed in claim 1, wherein the process comprises:
   a) feeding cracked hydrocarbon products from FCC riser-reactor to a main fractionator column to obtain a product stream comprising of dry gas, LPG, and light naphtha,
   b) separating the product stream in a gascon section, into LPG comprising of $C_3$ and $C_4$ hydrocarbons, and dry gas comprising hydrogen, methane, ethane, ethylene, and other non-condensable gases,
   c) routing the LPG stream to propylene recovery unit (PRU) to separate and obtain $C_4$ hydrocarbon stream from debutanizer section,
   d) routing the $C_4$ hydrocarbon stream to the $C_4$-separation section to separate and obtain $C_4$ alkanes comprising iso-butane and n-butane, wherein the iso-butane or n-butane or their mixture is used as feed stream for the ODH process,
   e) subjecting the flue gas from FCC regenerator to oxygen ($O_2$) separation to obtain the oxygen-free flue gas,
   f) premixing the $C_4$ feed stream obtained from step (d) and the oxygen-free flue gas from step (e) and utilizing the mixture as feed mixture for ODH process to obtain butylenes, unreacted butane(s), $C_2$, $C_3$, and other hydrocarbons,
   g) re-routing the products from step (f) to the gascon section after separation of water.

5. The process as claimed in claim 1, wherein the FCC process is fluid catalytic cracking or Resid fluid catalytic cracking or High severity fluid catalytic cracking or High severity propylene maximizing fluid catalytic cracking process.

6. The process as claimed in claim 1, wherein the ODH reactor is selected from a fixed bed or fluidized bed or moving bed or combination thereof.

7. The process as claimed in claim 1, wherein the alkane for dehydrogenation in the ODH process is selected from ethane, propane, and $C_4$ alkanes or any combination thereof.

8. The process as claimed in claim 1, wherein the dehydrogenation of ethane, propane and $C_4$ alkanes is carried out in the ODH process, wherein the $C_2$, $C_3$ and $C_4$ alkanes are separately introduced at different zones of a fluidized bed riser type of reactor, with continuous catalyst regeneration.

9. The process as claimed in claim 8, wherein the process comprises:
   a) sending the flue gas from the FCC regenerator to $O_2$ separation to obtain the oxygen-free flue gas,
   b) mixing the oxygen-free flue gas with ethane from ethylene recovery section and sending to feed mixture to the fluidized bed riser type of reactor;
   c) mixing the oxygen-free flue gas with the propane from PRU and sending feed mixture to the fluidized bed riser type of reactor;
   d) mixing the oxygen-free flue gas with $C_4$ alkanes from $C_4$-separation section and sending the feed mixture to the fluidized bed riser type of reactor;
   e) introducing the feed mixtures from step (b), (c), and (d) separately at different zones of the fluidized bed riser type of reactor to produce ethylene, propylene, and butylene;
   f) continuous circulation of catalyst from the reactor to catalyst regeneration unit;

g) re-circulating the hot catalyst to the reactor;

h) re-routing the products from step (e) to the gascon section after separation of water.

10. The process as claimed in claim 1, wherein the dehydrogenation of ethane, propane and iso-butane or n-butane occur simultaneously in separate reactors in series on a suitable catalyst which circulates from the former reactor to the latter with subsequent continuous catalyst regeneration.

11. The process as claimed in claim 10, wherein the process comprises:

a) sending the flue gas from the FCC regenerator to $O_2$ separation to obtain the oxygen-free flue gas, b) mixing the oxygen-free flue gas with the ethane from ethylene recovery section and sending the resultant feed mixture to a $C_2$ alkane dehydrogenation reactor to produce ethylene, wherein the feed mixture is pre-heated by $C_2$ alkane dehydrogenation reactor effluent stream, c) mixing the oxygen-free flue gas with the $C_3$ alkane product from PRU and sending the resultant feed mixture to a propane dehydrogenation (PDH) reactor to produce propylene, wherein the feed mixture is pre-heated by PDH reactor effluent stream, and d) mixing the oxygen-free flue gas with $C_4$ alkanes from $C_4$-separation section and sending the resultant feed mixture to a butane dehydrogenation (BDH) reactor to produce butylenes, wherein the feed mixture is pre-heated by BDH reactor effluent stream, e) continuous circulation of catalyst from $C_2$ alkane dehydrogenation reactor to PDH reactor and then PDH reactor to BDH reactor and then to catalyst regeneration unit;

f) re-circulating the hot catalyst to $C_2$ alkane dehydrogenation reactor;

g) re-routing the products from steps (b), (c) and (d) to the gascon section after separation of water.

12. The process as claimed in claim 2, wherein the feed mixtures comprise of at least one of ethane/oxygen-free flue gas, propane/oxygen-free flue gas, iso-butane/oxygen-free flue gas, and n-butane/oxygen-free flue gas, wherein the feed mixtures optionally comprise of diluents selected from steam, helium or a combination thereof.

13. The process as claimed in claim 2, wherein the alkane feed stream from the PRU is mixed with hot flue gas from first stage regenerator of resid FCC unit and the mixture is directly used as feed for ODH reactor to obtain a product stream comprising of hydrocarbons and non-condensable gases.

14. The process as claimed in claim 2, wherein the product stream is optionally routed to carbon monoxide (CO) recovery unit for separation of CO, wherein the CO deficient stream is recycled to the FCC gascon section.

15. The process as claimed in claim 1, wherein the integrated process enhances the yield of the propylene, butylenes, and ethylene by utilizing the oxygen-free flue gas from the FCC process.

16. The process as claimed in claim 3, wherein the heat from the flue gas exiting the FCC regenerator is utilized to pre-heat the ethane/oxygen-free flue gas, propane/oxygen-free flue gas, iso-butane/oxygen-free flue gas, and n-butane/oxygen-free flue gas feed stream prior to sending to ODH reactor.

17. The process as claimed in claim 3 wherein the heat from the products exiting the dehydrogenation reactor is utilized to pre-heat the ethane/oxygen-free flue gas, propane/oxygen-free flue gas, iso-butane/oxygen-free flue gas, and n-butane/oxygen-free flue gas stream with a heat exchanger.

* * * * *